US006258938B1

(12) United States Patent
Furie et al.

(10) Patent No.: US 6,258,938 B1
(45) Date of Patent: Jul. 10, 2001

(54) METHOD FOR THE PURIFICATION AND ISOLATION OF BLOOD CLOTTING PROTEINS USING CONFORMATION SPECIFIC ANTIBODIES

(75) Inventors: Bruce E. Furie; Barbara C. Furie, both of Wellesley; Howard A. Liebman, Newton, all of MA (US); Richard M. Lewis, Leesburg, VA (US)

(73) Assignee: NE Medical Center Hospital, Inc., Boston, MA (US)

( * ) Notice: Subject to any disclaimer, the term of this patent is extended or adjusted under 35 U.S.C. 154(b) by 0 days.

(21) Appl. No.: 07/931,563

(22) Filed: Aug. 18, 1992

Related U.S. Application Data

(63) Continuation-in-part of application No. 06/805,815, filed on Dec. 6, 1985, now abandoned, and a continuation-in-part of application No. 06/665,186, filed on Oct. 26, 1984, now abandoned, which is a continuation-in-part of application No. 06/546,364, filed on Oct. 28, 1983, now abandoned.

(51) Int. Cl.[7] .................................................. A61K 35/14
(52) U.S. Cl. ......................... 530/381; 530/383; 530/384; 530/413
(58) Field of Search ................................. 530/381, 383, 530/384, 413, 300

(56) References Cited

U.S. PATENT DOCUMENTS

| | | | |
|---|---|---|---|
| 4,000,098 | 12/1976 | Hofstee | 530/364 |
| 4,307,071 | 12/1981 | Murray et al. | 436/500 |
| 4,361,509 | 11/1982 | Zimmerman et al. | 530/383 |
| 4,386,025 | 5/1983 | Jordan | 530/393 |
| 4,454,106 | 6/1984 | Gansow et al. | 424/1.53 |
| 4,472,509 | 9/1984 | Gansow et al. | 436/508 |
| 4,474,690 | 10/1984 | Nylen | 530/413 |
| 4,769,320 | * 9/1988 | Furie et al. | 530/384 |
| 5,055,557 | * 10/1991 | Zimmerman | 530/381 |

OTHER PUBLICATIONS

Tai et al, (1980) *J. Biol. Chem.,* 255 2790–2795.
Goodall et al., (1982) *Blood,* 59, 664–670.
Furie et al., (1979) *J. Biol. Chem.,* 254, 9766–9771.
Lewis et al., (1983) *Biochem.,* 22, 948–54.
Fulcher et al., (1982) *Proc. Natl. Acad. Sci. USA,* 79, 1648–1652.
Nesheim et al., (1981) *Methods in Enzymol.,* 80, 249–274.
Fass et al., (1982) *Blood,* 59, 594–600.
Furie et al., (1978) *J. Biol. Chem.,* 253, 8980–87.
Madar et al., (1980) *J. Biol. Chem.,* 257, 8599–8605.
Furie et al., (1982) *Methods in Enzym.,* 84, 60–83.
Madar et al., (1980) *J. Biol. Chem.,* 257, 1836–44.
Tuddenham et al., (1979) *J.Lab. Clin. Med.,* 93, 40–53.
Rotblat et al., (1983) *J. Lab. Clin. Med.,* 101, 736–46.
Sperling et al. (1978) J. Biol. Chem. 253(11):3898–3906.*
Falb et al. (1976) in "Polymer Grafts in Brochemistry", Marcel Dekker, New York, pp. 197–221.*
Goodall et al. (Mar. 1982). Preparation of Factor IX Deficient Human Plasma by Immunoaffinity Chromatography Using a Monoclonal Antibody. Blood 59(3):664–670.*
Furie et al. (Oct. 10, 1979). Conformation Specific Antibodies as Probes of the γ–Carboxyglutamic Acid–Rich Region of Bovine Prothrombin. J. Biol. Chem. 254(19):9766–9771.*
Tuddenham et al. (1979). The Properties of Factor VIII Coagulant Activity Prepared by Immunoadsorbent Chromatography. J. Lab. Clin. Med. 93(1):40–53.*
Swanson et al. (Nov. 9, 1982), Vitamin K Dependent in Vitro Production of Prothrombin. Biochemistry 21(23):6011–6018.*

* cited by examiner

*Primary Examiner*—Christopher S. F. Low
(74) *Attorney, Agent, or Firm*—Fish & Richardson P.C.

(57) ABSTRACT

A method of isolating a protein from a mixture containing the protein, the method including providing an antibody immobilized on a solid support, which antibody is reactive with the protein complexed with a ligand and substantially unreactive with the protein not complexed with the ligand; contacting the mixture, in the presence of the ligand, with the immobilized antibody to bind the protein, complexed with the ligand, to the immobilized antibody to form an immune complex; and contacting the immune complex with a compound having a binding affinity for the ligand higher than the binding affinity of the protein for the ligand, to release the protein from the immobilized antibody.

19 Claims, 6 Drawing Sheets

METHOD FOR THE PURIFICATION AND ISOLATION OF BLOOD CLOTTING PROTEINS USING CONFORMATION SPECIFIC ANTIBODIES

This is a continuation of application Ser. No. 06/805,815, filed Dec. 6, 1985, now abandoned.

This application is a continuation-in-part of U.S. patent application Ser. No. 06/665,186, filed on Oct. 26, 1984 now abandoned, which in turn is a continuation-in-part of U.S. application Ser. No. 06/546,364, filed on Oct. 28, 1983 now abandoned.

BACKGROUND OF THE INVENTION

This invention was made in part with government support, and the government has rights in the invention.

This invention was made with Government support under Grant No. HL21543 awarded by the National Institutes of Health. The Government has certain rights in the invention.

The present invention is concerned generally with methods for the isolation of proteins, e.g., blood clotting proteins, from a mixture of proteins in a fluid. Proteins are commonly purified by immunoaffinity chromatography, in which a protein-containing mixture is contacted with an immobilized antibody to the protein, and the protein is then eluted using non-specific, harsh conditions to disrupt the protein-antibody complex.

One class of proteins for which immunoaffinity chromatography has been attempted are the proteins involved in the blood clotting-process. The general overall process of blood clotting involves two stages: an activation stage in which the proenzyme prothrombin, through the action of many Factors and calcium ions, is converted into its active enzyme form, thrombin, and a conversion stage in which the proteolytic enzyme thrombin acts upon fibrinogen to form fibrin, which forms a three dimensional network mesh that holds the formed elements of blood.

The requisite Factors for blood clotting are all proteins, several of which share some similarities in structure and function, while others are distinct moieties unlike any other. For example, six blood proteins (the "vitamin K-dependent proteins") require vitamin K for their complete synthesis: Factor IX, Factor X, Factor VII, prothrombin, protein S, and protein C. As a group, these proteins share marked homology in amino acid sequence, are activated by limited proteolysis from the zymogen to active enzyme form, and contain the novel metal binding amino acid γ-carboxyglutamic acid. These blood clotting proteins are representative of a unique class of metal-ion binding proteins which are able to bind a large number of bivalent and trivalent cations. Upon combination with metal-ion, such as calcium, magnesium, manganese and gadolinium ions, these proteins undergo a structural conformational transition involving changes in the peptide backbone and changes in exposure of specific amino acid residues, which can be monitored by fluorescence, circular dichroism, or immunochemical techniques.

Other blood clotting proteins also share this ability to bind with metal-ions. Factor V, proaccelerin, is essential in the conversion of prothrombin to thrombin and is a very labile protein which rapidly disappears from stored plasma. Factor VIII, antihemophilic factor, is essential for the making of thrombin and is deficient in the plasma of persons with classical hemophilia. Hemophilia is congenital and the blood of hemophiliacs appears normal relative to the coagulation mechanism except for the deficiency of Factor VIII.

The vitamin K dependent proteins are deficient, on an acquired basis, in liver disease, in vitamin K deficiencies and in the presence of vitamin K antagonist drugs such as sodium warfarin (Coumadin). Hemophilia B is a disorder characterized as a hereditary deficiency of Factor IX; of the 25,000 persons in the United States with hemophilia, approximately 10–12% are afflicted with Hemophilia B.

The treatment of persons whose disorders comprise acquired or congenital deficiencies of blood clotting proteins continues to be a high risk and costly therapy. For example, Hemophilia B is presently treated in two ways: use of fresh frozen plasma or use of a commercial preparation of Factor-IX. This latter material is a concentrate obtained by partial fractionation of normal human plasma and is, at best, only of intermediate purity. Both therapies, the frozen plasma and the impure Factor IX concentrate, present a significant risk of hepatitis to the patient, but the Factor IX concentrate presents a far greater risk of infection since it is prepared from pooled human plasma. Essentially all hemophiliacs receiving multiple transfusions of either of these plasma products have been exposed to hepatitis and show seriological evidence of such exposure. Clinically, most have some form of abnormal liver function. However, the impure Factor IX concentrate adds risk to major complications, such as disseminated intravascular coagulation, thrombosis, and hepatitis, among others, believed to be directly caused or aggravated by the impurities in the preparations. More recently, an increased risk for the development of the highly fatal Acquired Immune Deficiency Syndrome (AIDS) has been reported in patients with hemophilia who received plasma concentrates. Although plasma protein infusion therapy is still the treatment of choice in these disorders, it is clear the complications of such infusion therapy, caused directly by the impurities in the prepared product, diminish its use and effectiveness. For this reason, any method which would provide blood clotting plasma protein in concentrated form of substantial purity would eliminate or significantly reduce the undesirable medical complications of current infusion therapy. Such an advance would satisfy a long recognized need and provide additional advantages such that infusion therapy may be used regularly and prophylactically by hemophiliacs to reduce or eliminate the protein deficiencies associated with such disorders.

As mentioned above, general procedures are known for purifying blood clotting factors in plasma by passing the plasma through an affinity chromatographic column comprising inert matrix support, usually in the form of beads, such as Sepharose to which is bound the antibody to the factor it is desired to isolate. The factor specifically complexes with the fixed antibody and thereafter the factor (antigen) is eluted from the column. However, prior to this invention, it has been very difficult to obtain therapeutically useful purifications of the desired blood clotting factors by this process since the blood clotting factors are very difficult to elute successfully. This is because the chemical or physical conditions necessary to separate the antibody from the protein can destroy the function of the protein.

Accordingly, it would be highly desirable to provide a means for isolating proteins including individual blood clotting factors whereby both the structural and functional integrity of the protein can be retained and whereby the proteins can be recovered in quantity.

SUMMARY OF THE INVENTION

In general, the invention features highly effective methods for isolating proteins which undergo conformational changes (i.e., a change in tertiary structure) when complexed with ligands. The methods employ antibodies (either polyclonal or monoclonal) which either specifically react with protein-ligand complexes, and substantially fail to react with the protein in the absence of the ligand, or specifically react with ligand-free protein, and substantially fail to react with the protein complexed with the ligand. (Since the protein is generally stabilized by the ligand, the protein, complexed with the ligand, is sometimes referred to herein as a "ligand-stabilized" conformer.)

Where the antibody used in the method is specific for the ligand-stabilized protein to be isolated, the method involves immobilizing the antibody on a solid support and then contacting a mixture containing the protein with the immobilized antibody, in the presence of the ligand, to bind the ligand-stabilized protein to the immobilized antibody. To release the protein, the protein-antibody complex is contacted with a compound having a binding affinity for the ligand higher than the affinity of the protein for the ligand; this higher affinity compound removes the ligand from the protein, changing the protein's conformation so that the antibody no longer binds to it, and the protein is thus released. This releasing step is specific and is carried out under mild conditions, and thus provides a high degree of purification without the risk of denaturation and loss of function associated with the non-specific, harsh conditions under which proteins are conventionally eluted from immunoaffinity columns.

When, in the above method, the protein containing mixture is citrated plasma, the method preferably involves removing the calcium from the plasma, e.g., by dialysis against a buffer, and then adding to the plasma a non-calcium ligand, e.g., $Mg^{++}$, which induces a conformational change recognized by the antibody; the support is also pre-equilibrated with an $Mg^{++}$-containing buffer. After the plasma is passed through the column, and prior to elution, non-specifically bound proteins are removed by washing the support with NaCl of a concentration of at least 0.2M, more preferably at least 0.45M. Optionally, a non-ionic detergent, e.g., Tween 20, can be used following the NaCl washing step to remove any residual non-specifically bound proteins.

Where the antibody used in the method is specific for the non-ligand stabilized protein, the method involves immobilizing the antibody on a solid support and then contacting a mixture containing the protein with the immobilized antibody, in the absence of the ligand (or under conditions under which the ligand does not bind to the protein), to bind the protein to the immobilized antibody. To release the protein, the protein-antibody complex is contacted with the ligand, which changes the conformation of the protein so that it no longer binds to the antibody. As in the case of the method employing an antibody specific for ligand-stabilized protein, the releasing step is specific and mild, and thus non-denaturing.

The methods of the invention provide an additional very important advantage: proteins, e.g., proteins involved in human blood coagulation, are separated not only from other proteins in the mixture, but from viral contaminants as well. This is extremely important for hemophiliacs, who frequently contract hepatitis from conventional Factor VIII and Factor IX preparations.

In addition, the methods of the invention provide high purification in a few simple steps, and are susceptible to inexpensive automation and scale-up.

Figure 7:
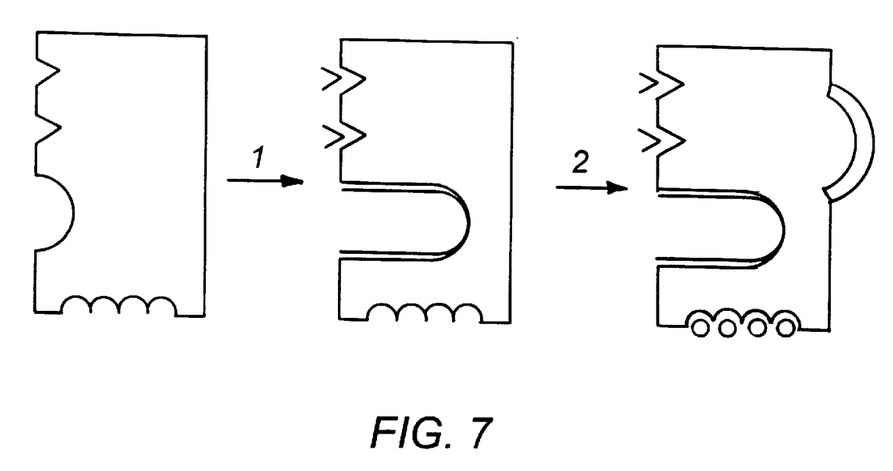
FIG. 7 is a diagrammatic illustration of the two transitional changes and three conformational states of prothrombin.

The invention also takes advantage of our additional discovery that native (i.e., fully carboxylated) gamma carboxylated proteins exist in three distinct conformational states in the presence of calcium ions. The protein is, in the first conformational state, uncomplexed with metal ions. The protein undergoes a first transitional change, from the first to the second conformational state, when calcium ions apparently bind to-the protein in a way which does not involve all of the gamma carboxyglutamic acid residues. When calcium ions tightly (but reversibly) bind to most or all of the gamma carboxyglutamic acid residues, the protein then undergoes the second transitional change, from the second to the third conformational state. Similar two-stage conformational transitions occur in the presence of $Sr^{++}$ and, to a lesser extent, $Ba^{++}$ and $Mg^{++}$ together, and $Ba^{++}$ and $Mn^{++}$ together. The discovery is illustrated diagrammatically in FIG. 7, which shows prothrombin in conformational states 1, 2, and 3. The first transitional change occurs when ions (triangles in FIG. 7) bind to the protein, and the second transitional change occurs when appropriate ions (circles in FIG. 7) occupy additional sites on the protein molecule.

Some divalent cations, e.g., $Mn^{++}$ and $Mg^{++}$, induce a first conformational change, but not a second. We have shown that antibodies can be made which will form immune complexes with proteins which have undergone a second transitional change, but which are substantially unreactive with those which have undergone only a first transitional change, or no change at all.

These discoveries are of great importance in the purification of gamma carboxylated proteins which are produced by cultured cells transformed with recombinant DNA encoding the protein, e.g., Factor IX, protein C, and prothrombin. Unlike normal human plasma, which contains only fully carboxylated, fully active protein (which can be purified, as described above, using any antibody specific for ligand stabilized protein), recombinant DNA-produced protein contains a mixture of non-carboxylated and poorly carboxylated protein (which has no activity), well-carboxylated protein (which has low activity), and fully-carboxylated protein (which is fully active). Many of the proteins in such a mixture are able, to some extent, to undergo a first transitional conformational change in the presence of divalent or trivalent cations, and thus an antibody which binds to the resulting second conformational form of the protein will undesirably purify from the mixture not just active, fully carboxylated protein, but partially and completely inactive protein as well. Thus an antibody which would function well in purifying active protein from normal human plasma could function poorly in purifying active material from recombinant cells and/or culture media.

We have found that this problem can be solved by employing in the purification of such recombinant DNA-produced proteins antibodies which bind to protein in a third conformational state, but not to protein in a second conformational state. Screening a heterogeneous mixture of antibodies for such third conformational state-specific antibodies takes advantage of the discovery, discussed above, that certain divalent ions induce only a first, but not a second, transitional change. The screening method for these antibodies is generally carried out as follows.

First, a column is provided containing immobilized protein complexed with an ion, e.g., $Mg^{++}$ or $Mn^{++}$, which is capable of inducing a first but not a second transitional change in the conformation of the protein, to give protein which is in a second conformational state.

There is then passed through the column a mixture of antibodies which have been raised to the protein. Those antibodies in the mixture which are capable of binding to the second conformational state of the protein do so on the column, and the antibody-containing material which does not bind to the column is thus free of such antibodies.

In the next step, the unbound antibody-containing material is passed through a column containing immobilized protein complexed with a cation, e.g., $Ca^{++}$, $Sr^{++}$, $Ba^{++}/Mn^{++}$, or $Ba^{++}/Mg^{++}$, capable of inducing a second transitional change in the protein, to give protein in a third conformational state. This column will be expected to contain protein exhibiting binding sites for second and third conformational state-specific antibodies, but only third conformational state-specific antibody will bind to the column, because antibody capable of binding to protein in a second conformational state has been removed in the previous column purification step.

After the antibody-containing material has been passed through the second column, the desired third conformational state-specific antibodies are eluted by contacting the protein-antibody complex with a compound (e.g., a chelating agent) which has a binding affinity for the divalent ion higher than the affinity of the protein for the divalent ion; this removes the cation from the protein, changing the conformation of the protein so that the antibody no longer binds to it, and the antibody is thus released from the column.

The third conformational state-specific antibody is then used to purify active, fully-carboxylated or nearly fully carboxylated protein from recombinant material (or from plasma) according to the method described above for ligand-stabilized protein isolation generally.

The invention further provides a composition which contains Factor IX of a specific activity of at least 125 units/mg, more preferably 150 units/mg; the composition is preferably substantially free of proteins other than Factor IX, is 95–100% homogeneous, and is free of Hepatitis B virus contamination.

Other features and advantages of the invention will be apparent from the following description of the preferred embodiments thereof, and from the claims.

DESCRIPTION OF THE PREFERRED EMBODIMENTS

The drawings will first be described.
Drawings

PROTEINS AND LIGANDS

The general method of the invention can be used to isolate any protein whose conformation is changed when the protein is complexed with a ligand.

One class of such proteins are the human and other mammalian plasma proteins involved in blood coagulation, i.e., Factors V, VII, VIII, IX, X, prothrombin, protein S, and protein C. These proteins undergo conformational changes when complexed with certain low molecular weight (<3,000) ligands, particularly divalent or trivalent metal ions such as $Ca^{++}$, $Mg^{++}$, $Mn^{++}$, $Co^{++}$, and $Gd^{++}$. Some of these proteins, e.g., prothrombin and Factor IX, have a metal ion binding site containing γ-carboxyglutamic acid, while others, e.g., Factor V, do not contain γ-carboxyglutamic acid, but nonetheless undergo a conformational change when complexed with a metal ion. The method of the invention which takes advantage of our discovery of three conformational states, above, is useful only in the purification of the γ-carboxylated proteins.

Other proteins which can be purified using methods of the invention are enzymes which can complex with a ligand to form a stable complex whose three-dimensional structure is different from that of the uncomplexed enzyme. Examples of such ligands are very poor substrates; suicide substrates (i.e., those substrates which are activated by the enzyme and form a convalent complex with the enzyme); substrate analogs which function as inhibitors; and enzyme inhibitors.
Antibody Production The antibodies used in the methods can be either polyclonal or monoclonal antibodies, produced by conventional techniques. The nature of the antigen used to generate the antibody depends on which of the general purification techniques is to be employed. If the antibody is to be specific for ligand-stabilized conformers, immunization is carried out using ligand-stabilized conformers of the protein or, if the ligand is already present in the immunized animal, the protein alone, without the ligand, can be used; the ligand present in the animal complexes with the immunizing protein in vivo, resulting in the production of antibodies to the ligand-stabilized conformers. For example, since calcium is present in animal blood, antibodies to $Ca^{++}$-stabilized human blood proteins such as Factor IX can be generated by immunizing with Factor IX not complexed with $Ca^{++}$. On the other hand, if the ligand is one not present in the plasma of the immunized animal, e.g., a substrate for an enzyme, immunization is carried out using the ligand-stabilized protein.

Where the protein isolation method employs an antibody specific for a non-ligand stabilized conformer of the protein, immunization can be carried out with the protein in the absence of the ligand if the ligand is not present in the immunized animal. If the ligand is present in the immunized animal (e.g., if the ligand is $Ca^{++}$ and the protein is a $Ca^{++}$-stabilizable human plasma protein such as prothrombin), immunization must be carried out using an antigenic analog of the protein which will not complex with the naturally-present ligand. In the case of the blood proteins which, in their normal state, have ligand binding sites containing γ-carboxyglutamic acid, immunization can be carried out using an abnormal, des-γ-carboxyglutamic acid form of the protein (in the case of vitamin K dependent proteins such as prothrombin and Factor IX, abnormal des-γ-carboxyglutamic acid forms of the proteins can be isolated from the blood of patients with vitamin K deficiency, patients treated with warfarin or other vitamin K antagonists, or from cells in cell culture secreting des-γ-carboxyglutamic acid forms of these proteins, particularly if vitamin K is not supplemented to the culture medium or a vitamin K antagonist is added). Alternatively, the immunizing antigen can consist of a peptide corresponding to a portion of the protein too small to complex with the ligand; if necessary, the peptide can be carried on a larger molecule such as bovine serum albumin or keyhole limpet haemocyanin.

Antibody Screening and Purification

Antibodies are screened for the ability to bind to one conformer or transitional state of the protein and not others, using screening techniques as described above. Antibodies are purified using affinity columns to which are bound the conformer of the protein to which the antibody is specific; elution is carried out with a compound having high affinity for the ligand, if the column contains antibody to the ligand-stabilized conformer, or with the ligand, if the column contains antibody to non-ligand-stabilized conformer. As described above, this procedure is a two step process when the desired antibody is specific for a third conformational state.

Binding to a Solid Support

The purified antibody is then bound to any conventional solid support used in protein purification techniques, e.g., an affinity chromatography column to which crosslinked agarose, polyacrylamides, or cellulose is attached via, e.g., cyanogen bromide, carbodiimide, or protein A. Conventional solid supports, e.g., various polymeric beads, used in non-chromatographic affinity purification methods can be used as well. The silica based Beckman Ultra-Affinity HPLC system can also be used.

Protein Isolation

Proteins are isolated by contacting a protein-containing mixture with the appropriate support-bound antibody, in the presence or absence of the appropriate ligand, depending on the method. Disruption of the immune complex is then achieved by changing the conformation of the bound protein, either by removing or adding the ligand. Where the bound protein is metal ion-stabilized, disruption is preferably achieved using a metal chelator such as EDTA, EGTA, citrate, oxalate, or phosphate.

The following specific examples are intended to more particularly point out the present invention, without acting as limitations on its scope.

PREPARATION OF PURIFIED HUMAN FACTOR IX CONCENTRATE

Preparation of Human Factor IX Antigen

Factor IX was isolated from fresh frozen human plasma by sequential barium citrate adsorption and elution, DEAE Sephadex chromatography, DEAE cellulose chromatography and heparin-Sepharose chromatography, according to the methods described in Rosenberg et al., (1974) *J. Biol. Chem.*, 250:1607–1617; and Miletich et al., (1978) *J. Biol. Chem.*, 253:6908–6916. The purified Factor IX migrated as a single band upon electrophoresis in polyacrylamide gels with dodecyl sulfate. Factor IX activity was determined with a two stage assay using Factor IX-deficient plasma, and was shown to have a specific activity of 180–200 units/mg.

Purified Factor IX was coupled to cyanogen bromide-activated Sepharose 4B at a concentration of 4.3 mg per ml of Sepharose (total volume 4 ml Sepharose).

Preparation of Anti-Factor IX:$Ca^{++}$ Antibodies

New Zealand white rabbits were immunized with Factor IX. Antibodies specific for metal-stabilized Factor IX (anti-Factor IX:$Ca^{++}$) were purified by affinity chromatography on the human Factor IX-Sepharose column (1.5×3 cm) as a modification of the technique of Tai et al. (1980) *J. Biol. Chem.*, 225:2790-2795, as follows. Antiserum was dialyzed overnight in 0.05 M Tris HCl, pH 7.4, 0.14 M NaCl, 3 mM $CaCl_2$, 0.05% $NaN_3$ (TBS/$CaCl_2$). The Factor IX-Sepharose column was equilibrated with the same buffer and the antisera was applied to the column. The column was exhaustively washed with the TBS/$CaCl_2$ to remove unbound protein. The anti-Factor IX:$Ca^{++}$ antibodies were eluted with TBS/5 mM EDTA. The bound anti-Factor IX antibodies which bind to Factor IX in the absence of metal ions were eluted with 4 M guanidine HCl.

The antibodies eluted with 5 mM EDTA (those specific for the $Ca^{++}$-stabilized Factor IX) were pooled and concentrated by ultrafiltration; these represented approximately 20% of the antibodies in the antiserum. Rabbit anti-Factor IX:$Ca^{++}$ antibody was coupled to cyanogen bromide-activated Sepharose 4B at a concentration of 3.3 mg per ml Sepharose (total volume 2 ml Sepharose) according to the method of Cuatrecasas et al. (1969) *PNAS USA*, 61:636–643; this antibody-Sepharose was used to purify Factor IX from plasma, as will be described in more detail below.

Preparation of Monoclonal Anti-Factor IX:$Ca^{++}$ Antibodies

Balb/c mice were immunized with 50 µg of human Factor IX antigen in complete Freund's adjuvant. These mice were then immunized biweekly with 25 µg of Factor IX in complete Freund's adjuvant for three months. Following a one month time period without any further immunization, these mice were injected with 25 ug of Factor IX in 0.15 M NaCl solution intravenously for the next three consecutive days prior to cell fusion.

Spleen cells (approximately $5 \times 10^7$ cells) from immunized mice were fused with the Sp2/0 plasma cell line ($5 \times 10^6$ cells in 28% polyethylene glycol 5000, Sigma Corporation) using the method of Kohler and Milstein [Kohler, G. et al., *Nature* (London), 256:495–497 (1975)]. Fused cells were suspended in complete medium comprising RPMI 1640, 15% Donor calf serum, 10 mM Hepes buffer, 4 mM glutamine and 20 µg/ml gentamycin and grown in this media for 48 hours. Fused cells were then removed from complete medium and resuspended in hypoxanthine-aminopterin-thymidine (hereinafter HAT) containing growth medium. The cell suspension was then distributed into individual dual wells of a microtiter tray as aliquots containing approximately $3 \times 10^5$ cells per well for continued cell growth. Supernatants from each well were assayed for anti-Factor IX antibody production after several weeks. Selected cell cultures were cloned by the limiting dilution method [McKearn, T. J. et al., *Monoclonal Antibodies*, Plenum Press, New York]. Although many clones were identified that produced monoclonal antibodies reactive with Factor IX, a single clone (designated HL 12-21) produced conformation-specific antibodies reactive with Factor IX only in the presence of metal-ions and not reactive with Factor IX in the absence of metal ions (clone HL 12-21 has since died).

Assay for Evaluation of Anti-Factor IX Antibody

A solid phase enzyme linked immunoabsorbent assay (ELISA) method was used for evaluating polyclonal rabbit and monoclonal murine anti-Factor IX:$Ca^{++}$ antibodies. An appropriate number of wells in microtiter plates were coated with human Factor IX at a 20 μg/ml concentration in 0.05 M borate (pH 8.5) for sixteen hours at 4° C. The plates were exhaustively washed with Buffer A (50 mM Tris HCl (pH 7.2), 0.14 N NaCl, and 0.05% $NaN_3$), and then Buffer A-containing 2% bovine serum albumin was added to the wells for thirty minutes at 24° C. After an extensive washing with Buffer A alone, 50 μl of tissue culture supernatant or polyclonal anti-Factor IX anti-serum was added to each respective well and then the plates incubated at 37° C. for one hour. Each well was then extensively washed with Buffer B comprising 50 mM Tris-HCl (pH 7.2), 0.14 N NaCl, 1.5 mM $MgCl_2$, 2 mM beta-mercaptoethanol, 0.05% $NaN_3$ and 0.05% Tween 20. Fab fragments of antimouse Ig (50 μl) raised in sheep and conjugated to beta-galactosidase was added in Buffer B to each well. After the plates were again incubated for two hours at 24° C., they were washed with Buffer B three more times. An enzyme substrate comprising p-nitrophenyl D-galactoside (50 μl in 0.05 M sodium phosphate, pH 7.2), 1.5 mM $MgCl_2$ and 100 mM beta-mercaptoethanol was added to each well and the reaction permitted to proceed for between thirty to sixty minutes at 24° C. The reaction product was monitored by measuring the absorbance at 405 nanometer (hereinafter nm) using a Dynatech MR 580 micro-ELISA autoreader.

For those studies evaluating the effect of calcium ions on antibody-Factor IX interaction, an additional step in the ELISA procedure was included. After incubation of monoclonal antibody with Factor IX coated wells, the plates were washed with a buffer comprising 50 mM Tris-HCl and 0.14 M NaCl, pH 7.2 containing either 10 mM EDTA or 5 mM $CaCl_2$. After two washings with the $CaCl_2$ or EDTA containing buffer, bound mouse immunoglobulin was detected and quantitated as described above.

In addition, in those experiments using polyclonal rabbit antibodies, anti-rabbit Ig (50 ml) raised in sheep and conjugated to alkaline phosphate was added in Buffer B without mercaptoethanol and this fluid added to the appropriate wells followed by incubation at 24° C. for two hours. After washing the wells in Buffer B, ρ-nitrophenyl phosphate disodium (50 μl in 1 M glycine, 1.5 mM $MgCl_2$, pH 10) was added to each well and the reaction was allowed to proceed for sixty minutes at 24° C. and stopped with 3 N NaOH. The reaction product was monitored and measured by absorbance at 405 nm.

Figure 1:
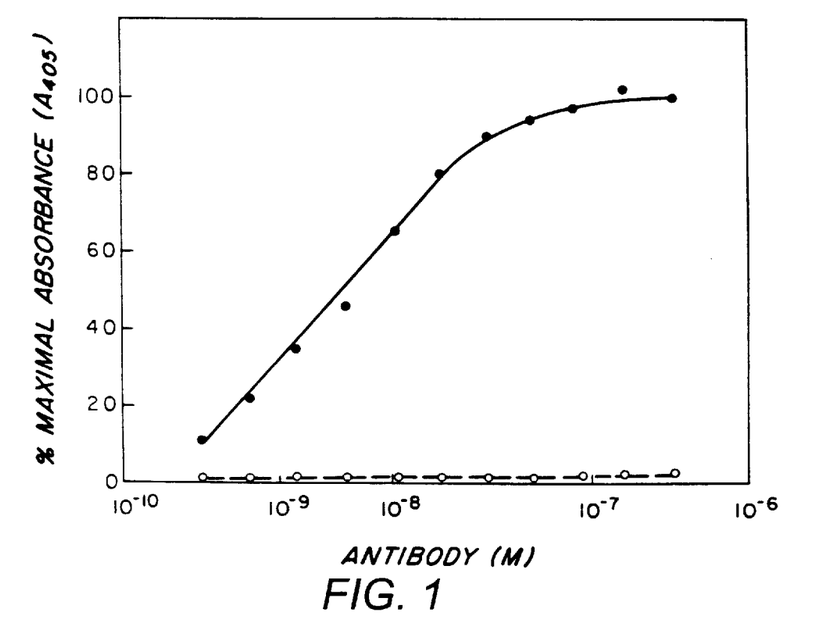
FIG. 1 is a graph illustrating the binding of anti-Factor IX:$Ca^{++}$ polyclonal rabbit antibodies to Factor IX in calcium chloride (●) and in ethylenediaminetetraacetic acid (EDTA) (○)
Figure 2:
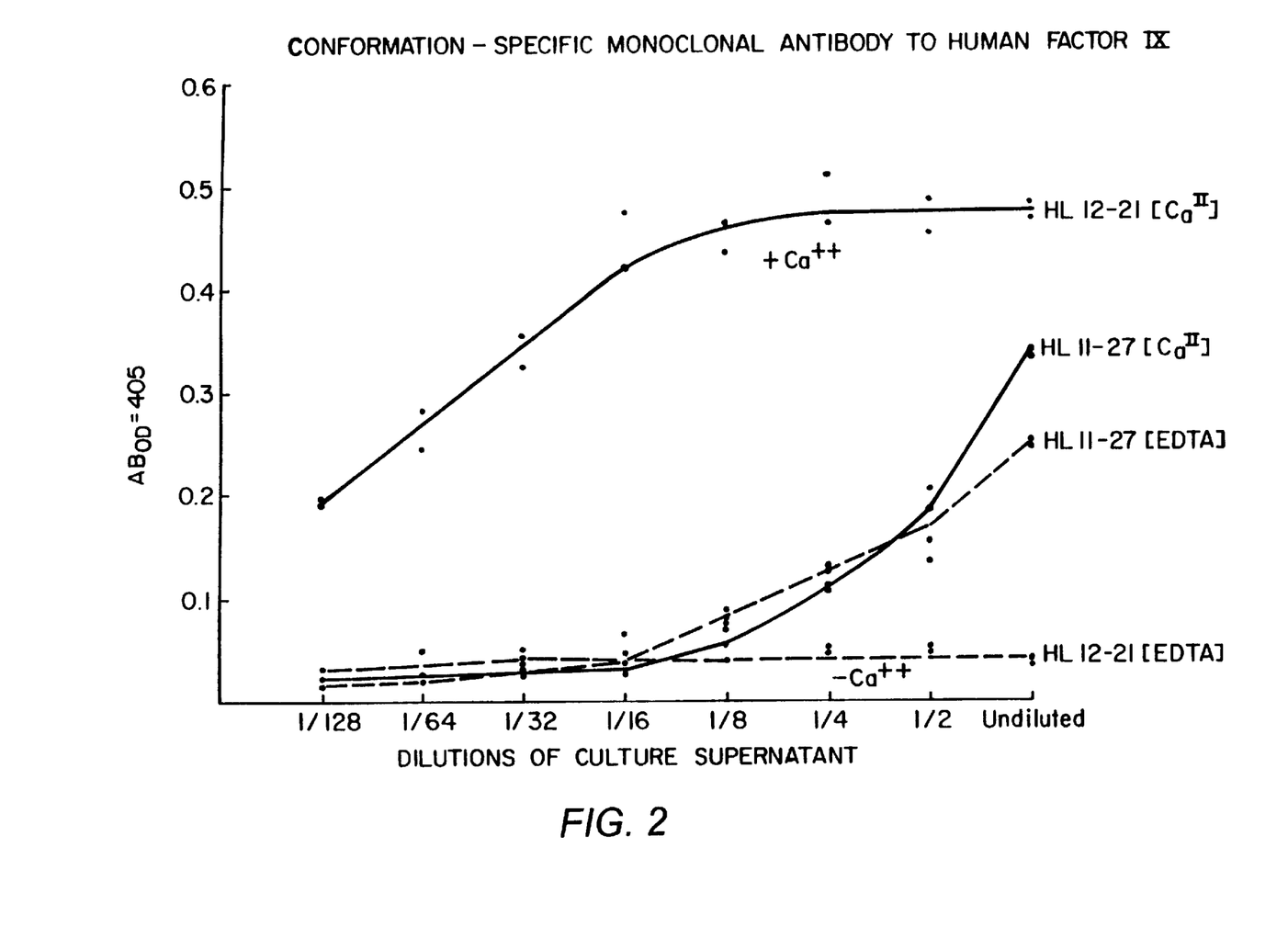
FIG. 2 is a graph illustrating the direct binding of anti-Factor IX:$Ca^{++}$ monoclonal antibodies (HL12-21) to Factor IX in the presence and absence of calcium chloride.

The results of evaluating polyclonal and monoclonal anti-Factor IX:$Ca^{++}$ antibodies are illustrated graphically in FIGS. 1 and 2. FIG. 1 demonstrates the binding capability of rabbit anti-Factor IX:$Ca^{++}$ polyclonal antibodies in the presence of either $CaCl_2$ or EDTA as is apparent therein, the ability of these antibodies to bind with Factor IX antigen is substantially reduced in the presence of EDTA. FIG. 2 illustrates the direct binding of HL 12-21 murine monoclonal antibody to Factor IX antigen in sequential dilution in the presence of calcium ion or EDTA. Specifically, one antibody clone, HL 12-21, reveals the inability of the monoclonal antibody to bind to Factor IX antigen in the presence of EDTA.

Evaluation of Antibody Specificity for Anti-Factor IX:$Ca^{++}$

Figure 3:
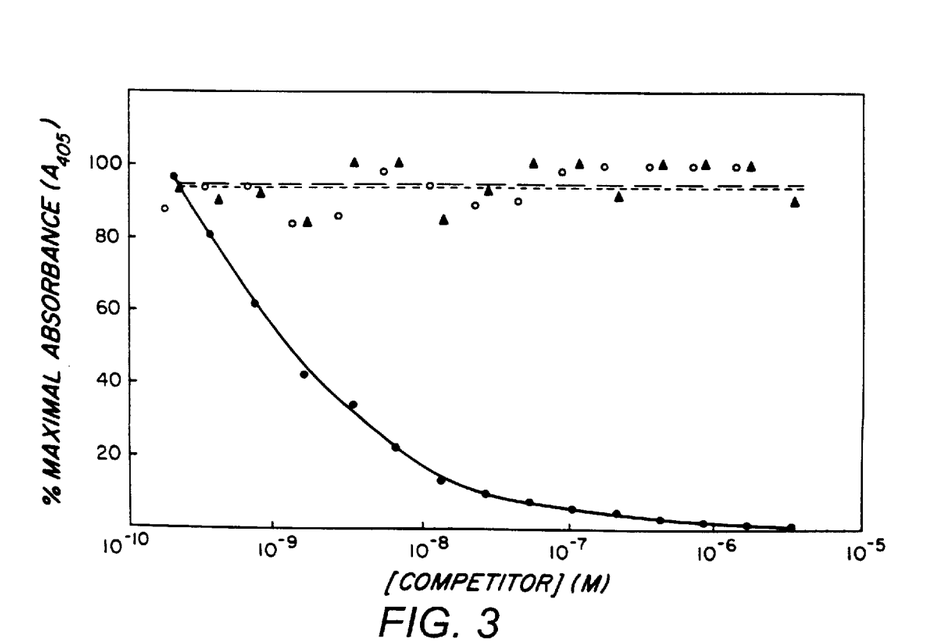
FIG. 3 is a graph illustrating the specificity of anti-Factor IX:$Ca^{++}$ polyclonal antibodies. Displacement is observed with Factor IX (●), but not with Factor X (△) or prothrombin (○).

The determination of antigenic specificity for anti-Factor IX:$Ca^{++}$ antigen murine monoclonal and rabbit polyclonal antibodies utilized two types of assays. The first assay employed microtiter plates whose wells were coated with either 20 ug/ml of human prothrombin, Factor X, or Factor IX. Individually, these plates were allowed to react with the antibodies. It was found that all of the antibody populations under test, the murine monoclonal anti-Factor IX:$Ca^{++}$ antibodies and the polyclonal anti-Factor IX:$Ca^{++}$ rabbit antibodies, reacted with and bound to the human Factor IX antigen exclusively. In the second assay (FIG. 3), human prothrombin, Factor X and Factor IX were added individually to separate wells at varying concentrations to a constant amount of murine monoclonal or rabbit polyclonal anti-Factor IX:$Ca^{++}$ antibody. Following an initial reaction time of 30 minutes, the reaction fluids from those wells were added to other microtiter wells coated with Factor IX antigen. The interaction of the initial reaction fluids containing anti-Factor IX:$Ca^{++}$ antibody with the other plasma proteins instead of immobilized Factor IX antigen was monitored as a decrease in the amount of immunoglobulin which bound to the immobilized solid phase containing Factor IX. The results are graphically illustrated in FIG. 3 in which rabbit polyclonal anti-Factor IX:$Ca^{++}$ antibodies bound poorly, if at all (less than 10,000×) with human prothrombin or Factor X, conclusively demonstrating the specificity of these antibodies for Factor IX in the presence of calcium ions.

Isolation of Purified Human Factor IX Using Anti-Factor IX:$Ca^{++}$ Antibody-Sepharose Matrix The purification of Factor IX was carried out as follows using the polyclonal anti-Factor IX: $Ca^{++}$-Sepharose described above. A Factor IX-enriched material was prepared by absorption of plasma (200 ml) to barium citrate, followed by elution of the vitamin K-dependent coagulation proteins as described in Rosenberg et al. (1974) J. Biol. Chem. 250, 1607. The barium citrate eluate (28 ml) was dialyzed for 16 hr in 0.05 M Tris·HCl, pH 7.4/0.5 M NaCl/0.02% Tween 20/0.05% $NaN_3$, and the anti-Factor IX—Ca($^{++}$)-Sepharose was equilibrated with the same buffer containing 7.5 mM $MgCl_2$. After dialysis, the barium citrate eluate was adjusted to 7.5 mM $MgCl_2$ and applied to the column (1.5×2 cm). The column was washed exhaustively with the equilibration buffer until all unbound protein was eluted. The Factor IX that bound to the column was eluted with 0.05 M Tris·HCl, pH 7.4/0.5 M NaCl/0.02% Tween 20/0.05% $NaN_3$/10 mM EDTA. The protein eluted with EDTA was concentrated in dialysis tubing ?O against sucrose and then dialyzed in Buffer A containing 1 mM benzamidine (pH 7.5) and 3 mM EDTA.

Purification of Factor IX from plasma was carried out by a similar experimental procedure. The plasma (190 ml) was dialyzed overnight into 0.05 M Tris·HCl, pH 7.4/0.5 M NaCl/0.02% Tween 20/0.05% $NaN_3$, and then brought to 7.5 mM $MgCl_2$ prior to application to the column. After the column was washed exhaustively with equilibration buffer, the bound Factor IX was eluted with the 10 mM EDTA buffer. This procedure can be performed without Tween 20 without significant effect on the purified protein product.

The recovered Factor IX was then dialyzed against 10 mM sodium phosphate, 0.14 N NaCl (pH 7.0) and then frozen at −70° C. The purified Factor IX was found to be structurally intact and functionally active.

Figure 4:
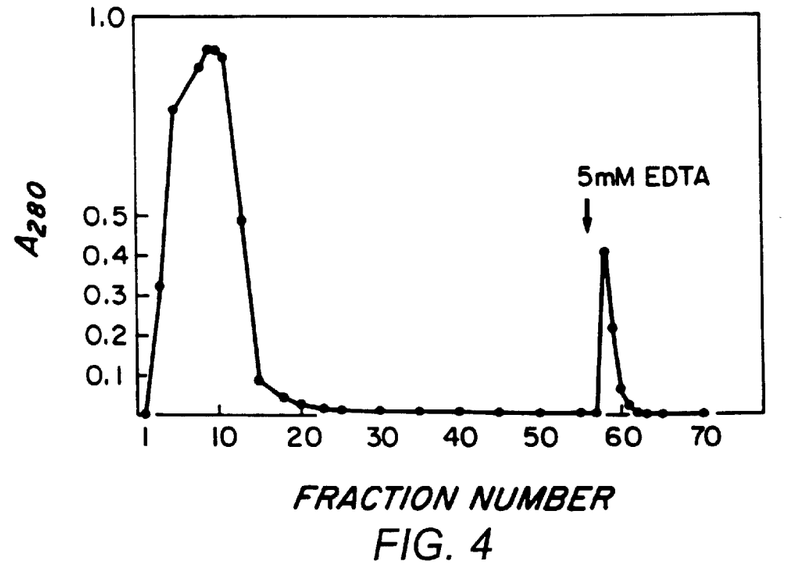
FIG. 4 is a graph illustrating the purification and isolation of human Factor IX from partially purified plasma using a method of the invention.

The purification of Factor IX from plasma as described above is graphically illustrated in FIG. 4. The purity of the Factor IX protein fraction eluted by the fluid containing EDTA (FIG. 4) was evaluated by electrophoresis in polyacrylamide gel containing dodecyl sulphate and compared to electrophoretic gels of the plasma applied to the affinity column and compared to the proteinaceous material eluted in flow-through in FIG. 4 which did not bind the column in the presence of $CaCl_2$ containing eluent. The specific activity of human Factor IX protein in the plasma was 0.013 units/mg of protein. After isolation of human Factor IX protein from an affinity matrix column comprising rabbit polyclonal anti-Factor IX:$Ca^{++}$ antibody using eluent containing EDTA, the specific activity (post dialysis) of the Factor IX protein was 124 units/mg. This approximately 10,000 fold increase in purity is greater than that obtained by any previously known single-step technique. This method removes most, if not all, of the contaminating Factor X and prothrombin activity as well as other proteins. The results are shown in Table 1 below. For reasons that are not yet entirely clear, much better results were obtained using the polyclonal antibody than using the monoclonal antibody.

If cross reactivity to Factor X or prothrombin or any other protein is observed, these cross reacting antibodies can be removed from the anti-Factor IX: $Ca^{++}$ antibodies by passage through a Factor X Sepharose or prothrombin-Sepharose column.

product from 20 to 10,000 times purer may be obtained. It will be appreciated by those skilled in this art that this methodology enlarged to commercial scale represents a major decrease in the cost of producing plasma infusion products and offers a superior product which will eliminate the undesirable medical complications presently accepted as a consequence of present plasma infusion therapy methods.

Separation of Factor IX from Hepatitis B Virus

Partially purified Factor IX concentrates used in the treatment of hemophilia B are associated with a high risk of hepatitis virus contamination. We questioned whether the purified Factor IX prepared by immunoaffinity chromatography would be free of viral contaminants. Ascites (1 ml) from a patient with primary hepatocellular carcinoma, rich in hepatitis B virus as measured by the assay of hepatitis B surface antigen, was added to fresh frozen plasma (200 ml). The Factor IX was purified by immunoaffinity chromatography, as described above, using anti-Factor IX:$Ca^{++}$-Sepharose. Viral surface antigen was measured by

TABLE 1

Purification of Human Factor IX

|  | Vol. | Total | Activity, units/ml | | | Specific activity, units/mg | | | % yield |
|---|---|---|---|---|---|---|---|---|---|
|  | ml | protein, mg | p | X | IX | P | X | IX | (total IX) |
|  | | | Experiment 1 | | | | | | |
| Barium citrate eluate | 28 | 142 | 2.3 | 3.0 | 2.9 | 0.5 | 0.6 | 0.6 | 100 |
| EDTA eluate | 3.9 | 0.4 | 0 | 0 | 15.9 | 0 | 0 | 151 | 77 |
|  | | | Experiment 2 | | | | | | |
| Plasma | 190 | 10,380 | 0.8 | 0.7 | 0.7 | 0.015 | 0.013 | 0.013 | 100 |
| EDTA eluate | 3.1 | 0.9 | 0 | 0 | 34.8 | 0 | 0 | 124 | 81 |

P = Prothrombin
X = Factor X
IX = Factor IX

The binding specificity of polyclonal or monoclonal anti-factor IX:$Ca^{++}$ was demonstrated by the application of purified human Factor X and prothrombin to the above-described anti-Factor IX: $Ca^{++}$ affinity matrix. Purified preparations of these vitamin K dependent coagulation proteins were dialyzed against Buffer A containing 1 mM $CaCl_2$ and 1 mM benzamidine (pH 7.5) and then applied to an affinity matrix column equilibrated with this dialysate. Unlike the Factor IX protein, which bound to the affinity matrix, the Factor X and prothrombin proteins were eluted by the dialysate fluid. The separation and individual elution of the respective plasma proteins from the affinity matrix was monitored by measuring the absorption at 280 nm. The functional activities of Factor X and prothrombin recovered in the initial elution fluid through the affinity matrix column were also assayed by testing each protein's ability to accelerate the clotting of bovine Factor X-VII or Factor II-VII deficient plasma using the Russell's viper venom-cephalin coagulation procedure.

Figure 6:
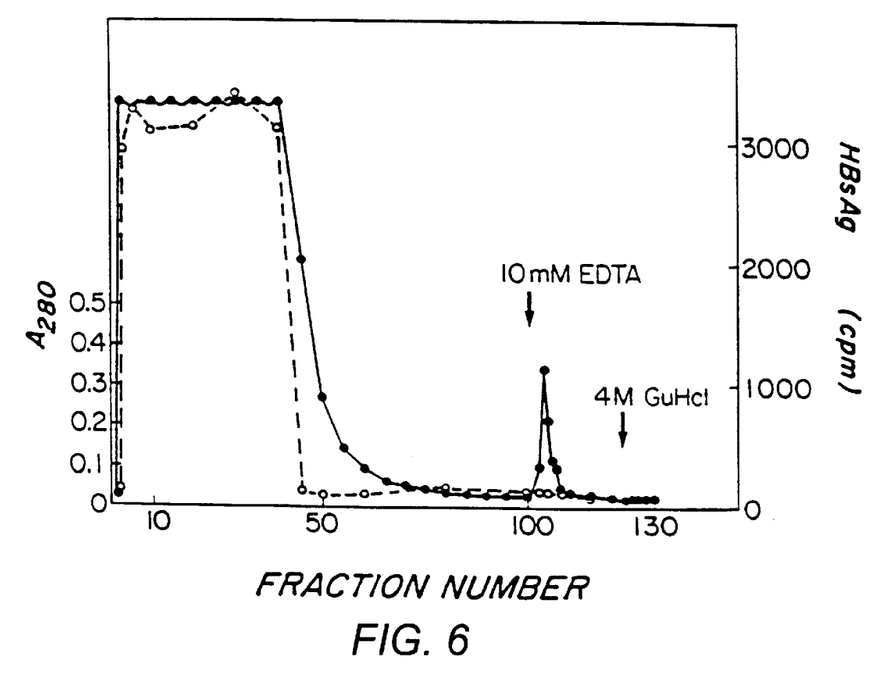
FIG. 6 is a graph illustrating the removal of Hepatitis B surface antigen from Hepatitis B virus-contaminated plasma, using a method of the invention. The column fractions were assayed for protein concentration (absorption 280 nm ●) and hepatitis B surface antigen (HBsAg ○) by competition radioimmunoassay. The quantitative presence of hepatitis virus is expressed as an increase in cpm in the RIA (non-specific binding is 124 cpm, positive samples greater than 250 cpm).

The major advantages offered by the method of purification described above for Factor IX include the following: concentrated preparations of marked purity, having between 95–100% homogeneity, are obtainable consistently using an affinity matrix purification procedure which is considerably simpler than the classical multi-step purification techniques presently known; in comparison to the presently available products for plasma infusion therapy and the Konyne®, Proplex®, or other commercial concentrate, a pure protein radioimmunoassay in column fractions. All of the hepatitis B surface antigen failed to bind to the affinity matrix. There was no detectable hepatitis virus in the EDTA eluate containing Factor IX (FIG. 6). After a 50-fold concentration of the Factor IX fractions no hepatitis virus was detectable. Within the limits of detection these results indicate that Factor IX is separated from hepatitis virus during its purification.

Separation of Factor IX from Culture Media of Recombinant Cells

As mentioned above, Factor IX only possesses its full biological activity in its fully carboxylated form. Third conformational state-specific antibodies, prepared as described above, can be immobilized on a column and used to purify this fully carboxylated Factor IX from the culture media of recombinant cells, which normally contains, along with fully carboxylated Factor IX, partially or wholly inactive Factor IX which is less than fully carboxylated.

Preparation of Purified Human Prothrombin Concentrate

Human prothrombin can be isolated using an immobilized antibody specific for-$Ca^{++}$-stabilized prothrombin, or using an immobilized antibody specific for abnormal, des-γ-carboxyglutamic acid prothrombin and unreactive with the $Ca^{++}$-stabilized prothrombin. The former antibody is made by immunization with prothrombin, the latter by immunization with abnormal prothrombin. As in the case of Factor IX purification, the first stage is the preparation of antigen for immunization.

Preparation of Prothrombin Antigen

Human prothrombin was prepared from fresh frozen plasma using established methods of protein precipitation used in sequence comprising: barium citrate adsorption, ammonium sulfate precipitation, ion exchange chromatography and dextran sulfate-agarose chromatography [Rosenberg, J. S. et al., *J. Biol. Chem.*, 250:1607–17 (1974) and Miletch, J. P. et al., *J. Biol. Chem.*, 253:6908–6914 (1978)]. The purified prothrombin obtained in this manner was shown to have specific activity of 10 units/mg by coagulation assay (Fullerton, K. W., *Lancet*, 2:195 (1940).

Preparation of Polyclonal and Monoclonal Anti-Prothrombin:$Ca^{++}$ Antibodies

Polyclonal conformation-specific antibodies to prothrombin were raised by immunization of New Zealand white rabbits in the manner described above for Factor IX. After collection of the blood by venipuncture and centrifugation, the serum fraction was used as the source of antibodies which were subsequently removed by affinity chromatography on a column matrix. The affinity matrix comprised prothrombin which had been covalently linked to cyanogen bromide-activated Sepharose using established methods. Anti-prothrombin:$Ca^{++}$ antibody was eluted from the affinity matrix using Buffer A containing EDTA.

The preparation of murine monoclonal conformation specific anti-prothrombin antibodies and the evaluation of such conformation specific antibodies generally using the ELISA methodology was carried out as described above for Factor IX.

The Evaluation of Monoclonal Antibody Specificity

The antigenic specificity of several monoclonal antibodies derived from those cloned identified as RL 1.3 and RL 1.9 were evaluated using a competitive assay based upon the ELISA methodology. Antibodies from these clones were shown to bind to immobilized human prothrombin; additional free prothrombin was then added which competed with the immobilized prothrombin for the antibodies. Using this competitive assay, the interaction of these monoclonal antibodies with prothrombin fragment 1, abnormal (des-γ-carboxyglutamic acid) prothrombin, thrombin, prothrombin 1 and bovine prothrombin were examined. The results demonstrated that both types of monoclonal antibodies (RL 1.3 and RL 1.9) bound fragment 1 (the $NH_2$-terminal third portion of prothrombin) while neither of these bound prethrombin 1 (the COOH-terminal two third portion of prothrombin). These antibodies did not bind at all to thrombin (which had been previously treated with p-amidinophenylmethanesulfonyl fluoride). Significantly, higher concentrations (ranging from 2-fold to 10-fold) of prothrombin fragment 1 compared to prothrombin were required to inhibit 50% of antibody-immobilized prothrombin interaction. In addition, neither of these monoclonal antibody types bound to bovine prothrombin.

Monoclonal antibodies from three hybridoma culture supernatants were then examined for prothrombin binding activity in the presence and absence of calcium ions. The clones RL 1.3, RL 1.9, and-HL 10.6 produced anti-prothrombin antibodies which bound prothrombin in the presence of 5 mM $CaCl_2$, but showed no significant binding in the presence of 10 M EDTA. Clone RL 1.3 has been deposited in the American Type Culture Collection (ATCC) and given ATCC Accession No. HB 8637. Applicants' assignee, New England Medical Center, acknowledges its responsibility to replace this culture should it die before the end of the term of a patent issued hereon, and its responsibility to notify the ATCC of the issuance of such a patent, at which time the deposit will be made available to the public. Until that time the deposit will be made available to the Commissioner of Patents under the terms of 37 CFR §1.14 and 35 USC §112.

Figure 5:
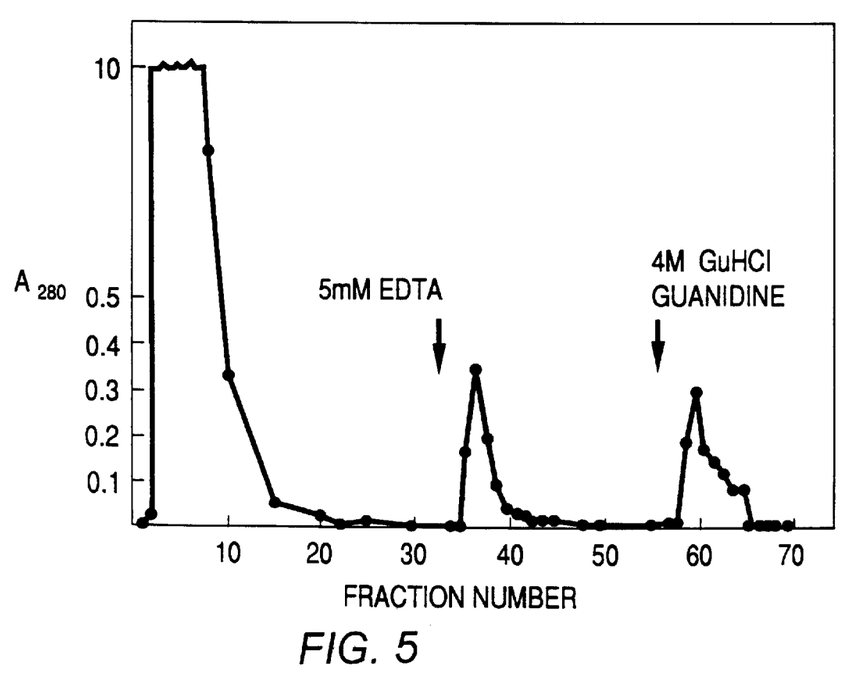
FIG. 5 is a graph illustrating the binding of anti-prothrombin:$Ca^{++}$ monoclonal antibody to prothrombin in the presence of calcium chloride and its elution with EDTA.

Purification of Anti-Prothrombin:$Ca^{++}$ Antibodies from a Monoclonal Antibody Pool Hybrid clones producing a variety of anti-prothrombin antibodies were grown in large volumes of culture fluid using established methods [Lewis, R. et al., *Biochemistry*, 22:948–954 (1983)]. Several types of antibodies were purified from a 50% ammonium sulfate fraction of such fluids by affinity chromatography. The antibody pool was applied to a 2×6 cm column affinity matrix comprising prothrombin covalently bound to agarose which was previously equilibrated with an eluent comprising Tris-HCl (pH 7.5), 0.5 M NaCl and 5 mM $CaCl_2$ (FIG. 5). The eluted fractions obtained after passage through this affinity matrix were monitored by measuring the absorbance of the fractions at 280 nm. After the affinity matrix was washed free of unbound protein, the bound protein fraction was eluted using an eluent comprising 0.05 M Tris-HCl (pH 7.5), 0.5 M NaCl and 10 mM EDTA. The proteins in this eluent were then dialyzed against a dialysate comprising 0.05 M Tris-HCl (pH 7.5), 0.15 M NaCl and 0.02% sodium azide for 16 hours and subsequently stored at −20° C.

Interaction of Anti-Prothrombin:$Ca^{++}$ Antibodies with Prothrombin

The interaction of monoclonal antibodies obtained from the RL 1.3 clone with prothrombin was studied using a wide range of calcium ion concentrations using the ELISA method. To eliminate contaminating calcium ion as a source of potential error in the assay, microtiter plates containing immobilized prothrombin were washed with a buffer containing EDTA and then exhaustively washed with a fluid comprising 0.05N Tris-HCl (pH 7.5) and 0.15 M NaCl prepared with metal-free water. The results demonstrated that all of the monoclonal antibody binding to the immobilized prothrombin was calcium dependent. Maximal binding was observed at a concentration of 0.9 mM $CaCl_2$ and half-maximal binding was observed at a concentration of 0.1 mM $CaCl_2$. Similarly, the binding of RL 1.3 antibodies to insolubilized prothrombin was measured in which varying concentrations of RL 1.3 anti-prothrombin antibody was added to a microtiter plate whose wells were coated with excess prothrombin. Using the empirical data obtained, a Scatchard plot was prepared in which the binding constant of monoclonal anti-prothrombin:$Ca^{++}$ antibody, $K_a$, was calculated to be $2.3 \times 10^9 M^{-1}$. It was noted that the binding curve was linear over the entire concentration range evaluated indicating that a single population of antibody combining sites was involved as expected for the monoclonal antibody preparation.

Preparation of Monoclonal or Oligoclonal Affinity Matrices for Isolation of Purified Prothrombin These monoclonal anti-prothrombin:$Ca^{++}$ antibodies are used to prepare an affinity matrix for the isolation of prothrombin protein which bind to calcium ions to form a calcium ion stabilized form of prothrombin. The methods used are similar to those described earlier in Example 1 regarding the use of polyclonal or monoclonal anti-Factor IX:$Ca^{++}$ affinity matrices. One major advantage of the hybridoma produced monoclonal anti-prothrombin antibodies is that distinctly different monoclonal antibody populations, each being conformation specific for the calcium ion-stabilized prothrombin, can be combined in defined portions to form an oligoclonal antibody pool which provide optimum prothrombin binding capabilities with subsequent elution with EDTA of the bound prothrombin as a purified molecule. This pool of oligoclonal antibodies is linked to cyanogen bromide-activated agarose in a manner identical to monoclonal or polyclonal antisera to form an affinity matrix. Prothrombin containing fluids or prepared fractions are then applied to the affinity matrix in the presence of 5 mM $CaCl_2$ following elution of the non-binding materials using calcium ion containing buffers; the affinity matrix is then washed with citrate buffer or an eluent containing 10 mM EDTA. The calcium ions in the metal-ion stabilized forms of prothrombin bound to the affinity matrix become preferentially bound to the citrate buffer or the EDTA, thus dissociating the prothrombin-anti-prothrombic complex on the surface of the affinity matrix. It will be appreciated that it is this preferential binding of the metallic cation, the calcium ion in this instance, to the EDTA or citrate buffer which causes the dissociation of the prothrombin-antibody complex and the concomitant dissociation of the metal-ion stabilized form of prothrombin concurrently.

Purification of Prothrombin Using Anti-Abnormal Prothrombin

Anti-abnormal prothrombin can be used to prepare an affinity matrix, as described above for anti-Factor IX and anti-calcium-stabilized prothrombin. The matrix can be prepared using either a polyclonal or a monoclonal antibody to abnormal prothrombin. One such monoclonal antibody, which is substantially unreactive with $Ca^{++}$-stabilized prothrombin, has been deposited in the ATCC and given ATCC Accession No. HB 8638. Applicant's assignee, New England Medical Center, acknowledges its responsibility to replace this culture should it die before the end of the term of a patent issued hereon, and its responsibility to notify the ATCC of the issuance of such a patent, at which time the deposit will be made available to the public. Until that time the deposit will be made available to the Commissioner of Patents under the terms of 37 CFR §1.14 and 35 USC §112.

Prothrombin-containing fluids can be applied to the matrix, in the absence of 5 mM $CaCl_2$, and the matrix washed to remove non-binding materials. The matrix is then washed with $CaCl_2$, which complexes with the prothrombin to form the conformer not recognized by the antibody, resulting in the release of the prothrombin.

Preparation of Third Conformational State Prothrombin-Specific Antibodies

Anti-prothrombin antibodies were purified from rabbit anti-human prothrombin antiserum by applying antiserum to a prothrombin-Sepharose column; anti-prothrombin antibody was eluted with 4M guanidine HCl, dialyzed against TBS, concentrated by ultrafiltration, and dialyzed in TBS containing 1 mM $MgCl_2$. The purified antibody was then applied to a prothrombin-Sepharose column equilibrated in TBS/1 mM $MgCl_2$.

Antibody which failed to bind to the column under the above conditions was collected, concentrated by ultrafiltration, dialyzed against TBS containing 1 mM $CaCl_2$, and then applied to a prothrombin-Sepharose column equilibrated in TBS containing 1 mM $CaCl_2$. Antibody which bound to the prothrombin-Sepharose was eluted with 3 mM EDTA and was termed third conformational state prothrombin-specific antibody.

Third conformational state prothrombin-specific antibody was also prepared by substituting 1 mM $MnCl_2$/1 mM $BaCl_2$ or 1 mM $MgCl_2$/1 mM $BaCl_2$ for 1 mM $CaCl_2$ in the third step of the above procedure.

Specificity of Anti-Prothrombin:$Ca^{++}$-Specific Antibody Binding

Figure 8:
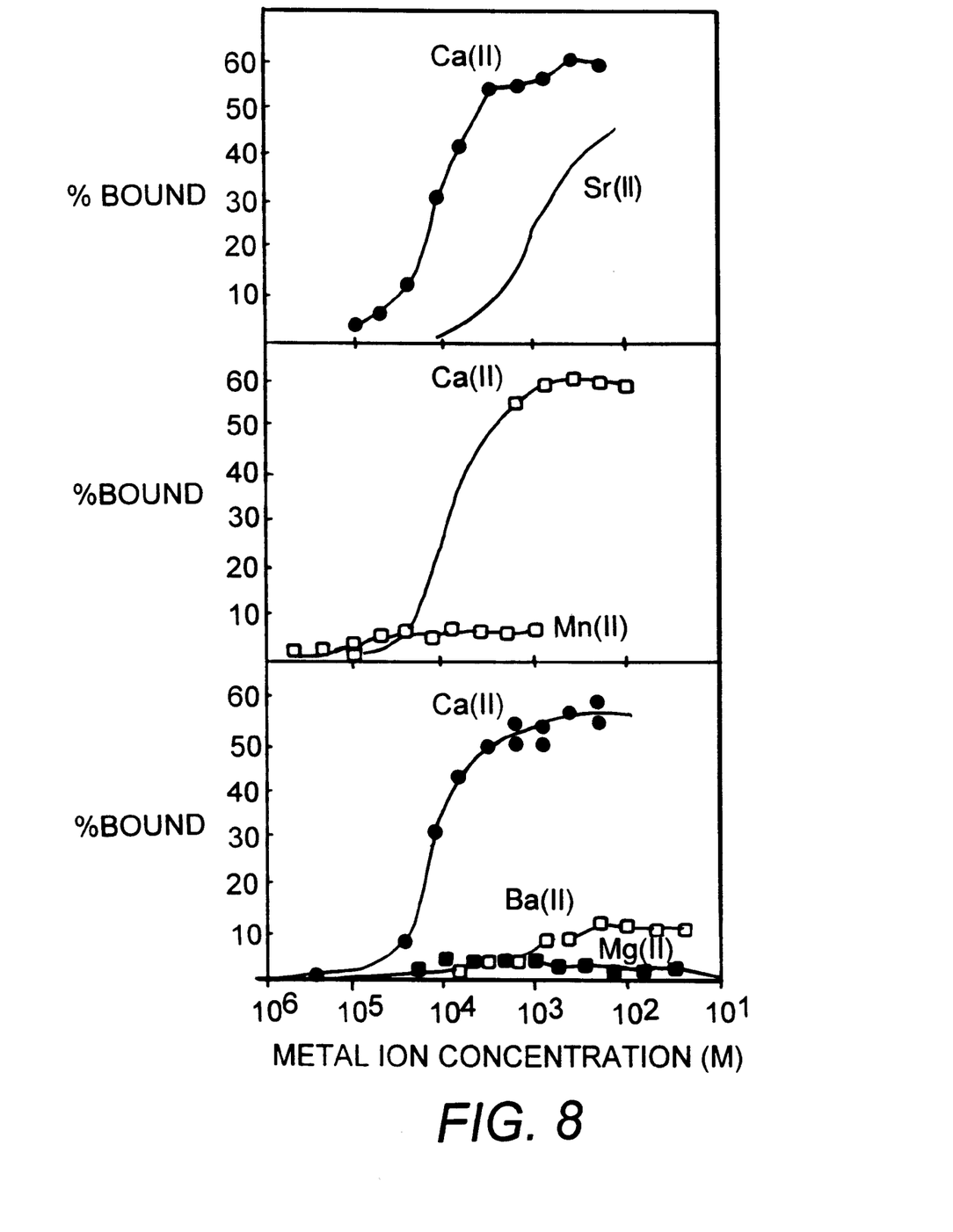
FIG. 8 is a graph illustrating the different binding properties of anti-prothrombin: $Ca^{++}$ to prothrombin in the presence of various metal ions.
Figure 9:
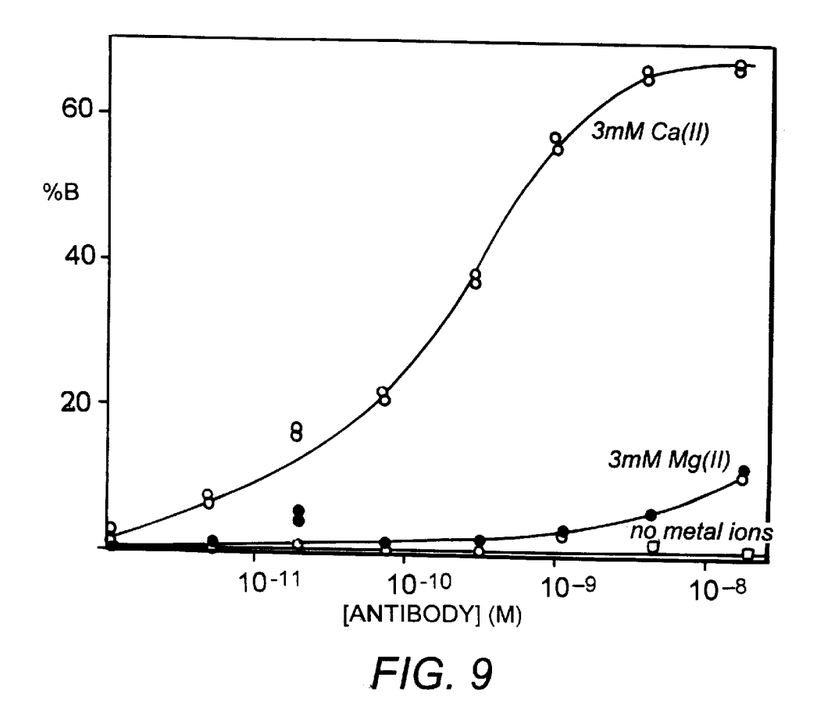
FIG. 9 is a graph showing the interaction between prothrombin and third conformational state-specific anti-prothrombin in the presence of calcium and magnesium ions.

The interaction of third conformational state prothrombin-specific antibody with prothrombin in the presence of various metal ions was studied using a direct binding radioimmunoassay and $^{125}$I-labeled prothrombin. In these experiments, the concentration of antibody and prothrombin were constant. The percentage of bound $^{125}$I-labeled prothrombin was determined as a function of metal ion concentration. As shown in FIGS. 8 and 9, Ca(II) supported antibody-prothrombin interaction. Half-maximal binding was observed at 0.1 mM $CaCl_2$. $SrCl_2$ also supported significant binding, with half-maximal binding observed at about 1 mM $SrCl_2$. $MnCl_2$ had little effect on antibody-prothrombin interaction, and $MgCl_2$ had no effect. $BaCl_2$ demonstrated a small but reproducible effect on the recognition of prothrombin by antibody. Half-maximal binding was observed at about 1 mM $BaCl_2$.

Effect of Metal Ion Combinations on Third Conformational State Prothrombin Specific Antibody Binding Most divalent and trivalent metal ions are capable of inducing the first of the sequential conformational transitions, although $Ba^{++}$ is less effective than other metal ions. The metal requirements for the second conformational transition, however, are highly selective, with $Ca^{++}$, $Sr^{++}$, and, to a lesser extent, $Ba^{++}$ being effective in inducing the second transition. The interaction of third conformational state prothrombin-specific antibodies with prothrombin in the presence of both Mn(II) and Ba(II) was evaluated; in principle Mn(II) should induce the first conformational transition and Ba(II) should induce the second conformational transition, thus exposing the same antigenic site that is expressed in the presence of Ca(II). As shown in a typical experiment depicted in Table 2, below, minimal antibody-prothrombin interaction was observed in the presence of 2.5 mM Ba(II) (1% Bound, 2.5 mM Mn(II) (2% Bound), or in the absence of metal ions (0.5% Bound). However, in the presence of both 2.5 mM Ba(II) and 0.1 mM Mn(II), significant antibody antigen binding was observed (14% Bound). Similar results were observed with 2.5 mM Ba(II)/1.0 mM Mn(II) (16% Bound). Approximately 80% of the prothrombin antigen was bound in the presence of Ca(II). These results suggest that certain combinations of metal ions are significantly more effective in inducing the second transition than these metal ions alone, although the antigen structure of the Ba(II)/Mn(II) or Ba(II)/Mg(II) stabilized prothrombin is not equivalent with that structure stabilized by Ca(II). These results lend further support for the concept that the second and third conformational states differ in their metal specificity.

TABLE 2

Effect of combinations of metal ions on supporting antibody-prothrombin interaction

| Metal ion | Concentration | % Bound |
|---|---|---|
| Anti-Prothrombin: Ca(II)-Specific Antibodies | | |
| Ca(II) | 1.0 | 80.0 |
| Ba(II) | 2.5 | 1.0 |
| Mn(II) | 2.5 | 2.0 |
| Mn(II)/Ba(II) | 0.1/2.5 | 14.0 |
| Mn(II)/Ba(II) | 1.0/2.5 | 16.0 |
| None | | 0.5 |
| Anti-Prothrombin: Mg(II)/Ba(II)-Specific Antibodies | | |
| Ca(II) | 1.0 | 75.0 |
| Mg(II) | 1.0 | 8.0 |
| Ba(II) | 1.0 | 5.0 |
| Mg(II)/Ba(II) | 1.0/1.0 | 31.0 |
| None | | 0.0 |

The binding properties of third conformational state prothrombin-specific antibody against prothrombin:$Mg^{++}$/

Ba$^{++}$ also were examined. As shown in Table 2, this antibody bound prothrombin minimally in the presence of Ba(II) or Mg(II). In combination, however, Ba$^{++}$/Mg$^{++}$ supported significant binding, although this level was still significantly lower than that produced by Ca(II). Although quantitative differences were observed when anti-prothrombin:Mg(II)/Ba(II)-specific antibodies were compared with anti-prothrombin:Ca (II) antibodies, it is likely that these populations are similar.

Inhibition of Prothrombin-Phospholipid Interaction with Conformation-Specific Antibodies If the third conformational state prothrombin-specific antibody against prothrombin:Ca(II) is directed against the phospholipid binding site on the prothrombin:Ca(II) complex, this antibody should inhibit the interaction of prothrombin with phospholipid vesicles. The binding of prothrombin to phospholipid vesicles in the presence of various antibody populations was compared using the relative 90° light scattering technique. The conditions chosen were those in which most of the prothrombin is antibody-bound. In the absence of antibody, prothrombin demonstrates the typical binding pattern. Preincubation with second conformational state prothrombin-specific antibody against prothrombin:Mg(II) did not inhibit prothrombin from binding the lipid vesicles. However, anti-prdthrombin:Ca(II)-specific antibody completely inhibited the binding of prothrombin to phospholipid vesicles. These results indicate that third conformational state prothrombin-specific antibody against prothrombin:Ca(II) is directed at or near the phospholipid binding site, and interferes with the interaction of prothrombin with lipid vesicles. In addition, these results suggest that the second conformational state prothrombin-specific antibody against prothrombin:Mg(II) binds to an antigenic determinant sufficiently distant from this phospholipid binding site such that bound antibody does not prevent prothrombin from binding to lipid vesicles.

Preparation of Third Conformational State Factor IX-Specific Antibodies

Anti-Factor IX antibodies were purified from rabbit anti-human Factor IX antiserum by applying 2 ml of antiserum which had been made 5 mM MgCl$_2$ to a Factor IX-Sepharose column (1.5×3 cm) equilibrated with TBS (pH 7.4)/5 mM MgCl$_2$. The column was washed exhaustively with TBS/5 mM MgCl$_2$ buffer to remove unbound antibodies. Those antibodies which failed to bind to the column in the presence of MgCl$_2$ were pooled, concentrated, and dialyzed into metal-free TBS containing Chelex 100, and then made 5 mM in CaCl$_2$ and applied to the Factor IX-Sepharose column (from which bound antibodies had been eluted) equilibrated with TBS/5 mM CaCl$_2$. The bound antibodies were eluted with TBS/7.5 mM EDTA and were termed third conformational state Factor IX-specific antibodies. Studies carried out as described above for prothrombin demonstrated that these antibodies bound to Factor IX in the presence of 5 mM CaCl$_2$, but exhibited no significant binding in the presence of 5 mM MgCl$_2$. Binding also occurred in the presence of SrCl$_2$, but not BaCl$_2$. There was small ((20% maximal) binding in the presence of MnCl$_2$ in high concentration.

Antibody Use

Antibodies specific for the third conformational state of any of the vitamin K-dependent proteins, in addition to their use in protein purification, can be used in immunoassays, e.g., to monitor warfarin therapy in warfarin-treated patients, whose blood characteristically contains such proteins (particularly, but not only, prothrombin) existing in various degrees of gamma carboxylation. Such immunoassays can be carried out using any of a variety of conventional methods, most of which involve contacting the sample with the antibody and measuring immune complexes as a measure of fully carboxylated protein-in the sample.

Other embodiments are within the following claims.

What is claimed is:

1. A method for isolating a vitamin K-dependent protein, which is complexed with a metal cation and exists in a stabilized conformational state, from a mixture containing said protein, said method comprising
   (a) providing an antibody immobilized on a solid support, said antibody being reactive with said protein complexed with a divalent or trivalent metal cation and substantially unreactive with said protein not complexed with said metal cation,
   (b) contacting said mixture, in the presence of said metal cation, with said immobilized antibody to bind said protein, complexed with said metal cation, to said immobilized antibody to form an immune complex, and
   (c) contacting said immune complex with a compound having a binding affinity for said metal cation higher than the binding affinity of said protein for said metal cation, to remove said metal cation from said protein to induce a non-stabilized conformational state of said protein and thereby release said protein from said immobilized antibody.

2. The method of claim 1 wherein said protein is a mammalian protein involved in blood coagulation.

3. The method of claim 1 wherein said cation is Ca$^{++}$, Mn$^{++}$, Co$^{++}$, Gd$^{++}$, or Mg$^{++}$.

4. The method of claim 1 wherein said higher binding affinity compound is a metal chelating agent.

5. The method of claim 1 wherein said protein contains γ-carboxyglutamic acid, and said metal cation complexes with said protein at a binding site containing said γ-carboxyglutamic acid.

6. The method of claim 1 wherein said protein is one of the mammalian proteins, Factor VII, Factor IX, Factor X, prothrombin, protein C, or protein S.

7. A method for isolating a vitamin K-dependent protein, which is uncomplexed with any metal cations and exists in a non-stabilized conformational state, from a mixture containing said protein, said method comprising
   (a) providing a conformation-specific antibody immobilized on a solid support, said antibody being reactive with said uncomplexed protein in a non-stabilized conformational state and substantially unreactive with said protein complexed with a metal cation in a stabilized conformational state,
   (b) contacting said mixture, under conditions under which no metal cation forms a complex with said protein, with said immobilized antibody to bind said protein to said immobilized antibody to form an immune complex, and
   (c) contacting said immune complex with metal cation can complex with said protein to induce a stabilized conformational state of said protein, and thereby release said protein from said immobilized antibody.

8. The method of claim 7 wherein said protein is a mammalian vitamin K-dependent protein.

9. The method of claim 7 wherein said cation is Ca$^{++}$, Mn$^{++}$, Co$^{++}$, Gd$^{++}$, or Mg$^{++}$.

10. The method of claim 7 wherein said protein has a metal cation binding site containing γ-carboxyglutamic acid, and said metal cation complexes with said protein at said binding site.

11. The method of claim 7 wherein said protein is one of the mammalian proteins, Factor VII, Factor IX, Factor X, prothrombin, protein C, or protein S.

12. The method of claim 1 wherein said protein is capable of forming three conformational states in the presence of said metal cation, and said antibody is capable of forming an immune complex with one of said conformational states and is substantially unreactive with the other two of said conformational states.

13. The method of claim 1 wherein said mixture comprises citrate-containing plasma and, prior to step (b), said plasma is treated to remove calcium from said plasma, said metal cation being a metal cation other than calcium.

14. The method of claim 13 wherein said ligand is $Mg^{++}$.

15. The method of claim 13 wherein, between steps (b) and (c), said solid support is washed with NaCl of a concentration of at least 0.2 M to remove from said support non-immunogenically bound protein.

16. The method of claim 15 wherein, between steps (b) and (c), said support is washed with a non-ionic detergent to remove from said support non-immunogenically bound proteins.

17. The method of claim 15 wherein the concentration of said NaCl is at least 0.45 M.

18. The method of claim 13 wherein said calcium removal is carried out by dialyzing said plasma against a buffer.

19. The method of claim 12 wherein said mixture is derived from recombinant cells.

* * * * *